United States Patent [19]

Grill et al.

[11] Patent Number: 4,883,861

[45] Date of Patent: Nov. 28, 1989

[54] CYSTEINE-RICH PEPTIDES HAVING GAMMA-GLUTAMIC ACID AND BETA-ALANINE UNITS, A PROCESS FOR THEIR PREPARATION AND THEIR USE

[75] Inventors: Erwin Grill; Ernst-Ludwig Winnacker; Meinhart H. Zenk, all of Munich, Fed. Rep. of Germany

[73] Assignee: Consortium für Elektrochemische Industrie GmbH, Munich, Fed. Rep. of Germany

[21] Appl. No.: 26,833

[22] Filed: Mar. 17, 1987

[30] Foreign Application Priority Data

Apr. 23, 1986 [DE] Fed. Rep. of Germany ....... 3613758

[51] Int. Cl.$^4$ .......................... C07K 7/02; C07K 7/10
[52] U.S. Cl. .................................. 530/326; 530/327; 530/328; 530/329; 530/330; 514/6; 514/13; 514/18; 424/131
[58] Field of Search ............... 530/370, 326, 330, 331, 530/327, 328, 329; 514/6, 13, 18; 424/131

[56] References Cited

U.S. PATENT DOCUMENTS

| | | | |
|---|---|---|---|
| 2,711,989 | 6/1955 | Laufer et al. ................... | 530/331 |
| 2,723,973 | 11/1955 | Herrick et al. ................... | 530/331 |
| 2,900,375 | 8/1959 | Amiard et al. ................... | 530/331 |
| 2,938,023 | 5/1960 | Weygand ....................... | 530/331 |
| 4,216,143 | 8/1980 | Ashmead ....................... | 530/370 |
| 4,725,670 | 2/1988 | Grill et al. ...................... | 530/328 |
| 4,758,551 | 7/1988 | Meister et al. ................... | 514/18 |

FOREIGN PATENT DOCUMENTS 0028124  3/1978  Japan ..................................... 514/6

OTHER PUBLICATIONS

Chem. Abstracts, vol. 67, 1967, 18111e.
Chem. Abstracts, vol. 103, 1985, 156965z.
Chem. Abstracts, vol. 105, 1986, 1535582.

*Primary Examiner*—Lester L. Lee
*Assistant Examiner*—T. Wessendorf
*Attorney, Agent, or Firm*—Collard, Roe & Galgano

[57] ABSTRACT

Disclosed are peptides which have the following amino acid sequence:

$$(\gamma\text{-Glu-Cys})_n\text{-}\beta\text{-Ala}$$

n being an integer from 2 to 11;
γ-Glu represents γ-glutamic acid;
Cys represents cysteine; and
β-Ala represents β-alanine.

A process for the preparation of these peptides is disclosed as well as processes for their use for the maintenance of hemeostasis in physiological systems, the diagnosis of tumors, and the removal of heavy metals from a chemical or physiological system which has been contaminated with heavy metal.

4 Claims, No Drawings

CYSTEINE-RICH PEPTIDES HAVING GAMMA-GLUTAMIC ACID AND BETA-ALANINE UNITS, A PROCESS FOR THEIR PREPARATION AND THEIR USE

The present invention relates to cysteine-rich peptides having γ-glutamic acid and β-alanine units.

Cysteine-rich proteins of animal original (metallothioneines) are presently known to the art. The amino acids of these proteins are linked together by α-peptide bonds. These metallothioneines are able to bind considerable amounts of heavy metal and, thus, presumably serve to detoxify in an organism correspondingly exposed. (In this context, see, Kägi *J. Biochem.* 89, 1839 (1981)).

In addition, peptides of the formula
H-γ-Glu-Cys-γ-Glu-Cys-Gly-OH, and
H-γ-Glu-Cys-γ-Glu-Cys-γ-Glu-Cys-Gly-OH,
which are obtained from fission yeast, have also been disclosed in *Agric. Biol. Chem.* 49, 71 (1985). Also known to the art are phytochelatins which can be obtained from higher plants and fungi and which are described by the following amino acid sequence: (γ-Glu-Cys)$_n$-Gly, wherein n is an integer from 4 to 7; in *Science* 230, 674 (1985) and *FEBS Letters* 197, 115 (1986).

The invention, more particularly, relates to peptides, also referred to as homo-phytochelatins hereinafter, which are characterized by the following amino acid sequence:

(γ-Glu-Cys)$_n$-β-Ala, wherein, n is an integer from 2 to 11, γ-Glu represents γ-glutamic acid, Cys represents cysteine, and β-Ala represents β-alanine.

The peptides according to the invention can be represented by the following structural formulae:
n=2 γ-Glu-Cys-γ-Glu-Cys-β-Ala
n=3 γ-Glu-Cys-γ-Glu-Cys-γ-Glu-Cys-β-Ala
n=4 γ-Glu-Cys-γ-Glu-Cys-γ-Glu-Cys-γ-Glu-Cys-β-Ala
n=5 γ-Glu-Cys-γ-Glu-Cys-γ-Glu-Cys-γ-Glu-Cys-γ-Glu-Cys-β-Ala
n=6 γ-Glu-Cys-γ-Glu-Cys-γ-Glu-Cys-γ-Glu-Cys-γ-Glu-Cys-γ-Glu-Cys-β-Ala
n=7 γ-Glu-Cys-γ-Glu-Cys-γ-Glu-Cys-γ-Glu-Cys-γ-Glu-Cys-γ-Glu-Cys-γ-Glu-Cys-β-Ala
n=8 γ-Glu-Cys-γ-Glu-Cys-γ-Glu-Cys-γ-Glu-Cys-γ-Glu-Cys-γ-Glu-Cys-γ-Glu-Cys-γ-Glu-Cys-β-Ala
n=9 γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-β-Ala
n=10 γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-β-Ala
n=11 γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-γ-Glu-Cys-β-Ala.

The invention further relates to homo-phytochelatins containing metal cations. In principle, all metal cations which are able to form coordinate bonds with the thiolate groups in the relevant homo-phytochelatin are suitable. Examples of these are, in particular, the cations of the metals leads, tin, bismuth, titanium, vanadium, molybdenum, manganese, cobalt, nickel, iron, copper, silver, gold, platinum, palladium, zinc, cadmium, mercury, uranium, arsenic, selenium, technetium and gallium.

The metal content, of course, depends on the valency of the cation which is coordinately bonded to the thiolate groups. The metal content amounts to 1 to 4 moles, normally 2 moles for divalent cations, per mole of homo-phytochelatin.

The homo-phytochelatins, according to the invention, can be obtained by extraction of plant material. Suitable plant materials are species which contain homo-glutathione, in particular, species of the superorder Fabales of the higher plants.

The following may be mentioned by way of example: plant material from the superorder of Fabales, in particular:
*Phasaeolus vulgaris* with its cultivars;
*Phasaeolus coccineus;*
*Phasaeolus aureus;*
*Phasaeolus lunatus;*
*Phasaeolus multiflorus;*
*Glycine max* (soybean);
*Erythrina crista-galli;* and
*Ononis atrix;*
*Lotus ornithopodiodes;*
*Trigonella coerulea;*
*Medicago sativa;*
*Melilotus alba;*
*Trifolium pratense;*
*Lathyrus ochrus;*
*Cicer avietinum;*
*Lens culinaris;*
*Astragalus lusitanicus;* and
*Galega officinalis.*

The plant material which is preferably used in cell cultures of these plants. However, it is also possible to use the differentiated plants or parts of plants for obtaining the peptides according to the invention.

The formation of the homo-phytochelatins in the plant is induced by treating the plants with metal or with metal salts. This treatment can be effected by any suitable manner in which the plants are able to take up the metals or metal cations. The induction of the homo-phytochelatins is preferably effected by treating cell cultures with solutions of metal salts in an aqueous system. This procedure generally entails cultivating the plant cell material in a solution of metal salt in which the metal concentrations are maintained at a level below that which would result in acute phytotoxicity. The lower limit of the metal concentration is 1 umole per liter. The upper limit depends, as already mentioned, greatly on the phytotoxicity of the appropriate metal cation. It may amount to as much as 100 mmoles per liter. The preferred range is from 10 μmoles per liter to 1 mmole per liter.

For this reason, the plant material which is preferably used for obtaining the homo-phytochelatins is that which has been cultivated, as described heretofore, in the presence of metals or metal cations or metal anions. The plant material is extracted by conventionally known methods for extracting peptides from plants. The procedure normally breaks down the cell culture of the plants. For this purpose, the plant material is expediently frozen, for example with liquid nitrogen, optionally comminuted, and finally taken up in a weakly alkaline aqueous preparation. The pH of the aqueous preparation is advantageously 7.5–9.5. However, it is also possible to use acidic preparations of pH 1-3. Suitable buffer solutions are often used as aqueous preparations for the foregoing pH ranges. The extract is worked up, optionally, after removal of non-disrupted plant material. It is advantageous for the extract first to be concentrated. This can be brought about, for example, by freeze-drying or by adsorption of the peptides on an ion exchanger followed by elution. Thereafter the proteins, which have been co-extracted, are precipitated by addition of an electrolyte (for example, an ammonium sulfate solution). During precipitation, the peptides according to the invention remain in solution. Finally, further purification steps can be carried out, such as, for example, ultrafiltration, gel filtration or precipitation of the homo-phytochelatins with copper sulfate solution. The selection of the eluates can, in each case, be based on UV measurements according to the criterion of the typical absorption band for the metal-thiolate bond and, optionally, by qualitative detection of the SH groups (for example, using Ellman's reagent).

Where the plant material has been taken up in a basic medium the phytochelatins are obtained with a corresponding content of metal ions. The free peptides can be obtained by, for example, acidification and precipitation (for example $H_2S$ precipitation) of the metal cations. Alternatively, it is also possible to use, for example, complexing agents (for example, ethylenediaminetetraacetates) to remove the metal content from peptides loaded with metal cations.

If the plant material is taken up in acidic preparations, the peptides are obtained without a content of metal cations.

The peptides according to the invention have the formula

$(\gamma\text{-Glu-Cys})_n\text{-}\beta\text{-Ala}$ and are, as a rule, obtained as mixtures; the main component among the peptides, according to the invention, usually being the peptide

$(\gamma\text{-Glu-Cys})_2\text{-}\beta\text{-Ala}.$

The content thereof is usually 2-8 times that of the longer-chain peptides.

The typical frequency distribution of the peptides, according to the invention, in the peptide mixture, based on the total amount of peptides is evident from the following data:

40-60 mole% $(\gamma\text{-Glu-Cys})_2\beta\text{-Ala}$
20-40 mole% $(\gamma\text{-Glu-Cys})_3\beta\text{-Ala}$
10-20 mole% $(\gamma\text{-Glu-Cys})_4\beta\text{-Ala}$
2-10 mole% $(\gamma\text{-Glu-Cys})_5\beta\text{-Ala}$.

The members with n=6-11 are usually present in only 1-0.001 mole%. If desired, it is possible to separate the peptides by known methods of peptide fractionation. Examples of these such methods are HPL chromatography, gel filtration, chromatography on ion exchangers, among others.

The peptides, according to the invention, can be used singly or in a mixture, in substance or in the form of a preparation which has also already been used for the formulation of peptide compositions hitherto. For example, it is possible for the peptides according to the invention to be physically sorbed or chemically adsorbed onto carrier materials in a conventially known manner. Examples of carrier materials are alginates, agaroses having functional groups (such as, for example, oxirane group), cellulose, polyacrylic resins, glasses, silicates, among others.

The peptides according to the invention are used in the form of pharmaceutical preparations for the treatment of acute and chronic heavy-metal poisoning. On the other hand, is also possible to use the peptides of the present invention, which are loaded with metal cations, to treat manifestations of metal deficiency or to maintain homeostasis of the relevant metals (for example, iron, zinc, copper). Other uses emerge from the environmental protection sector, for example, for clarification of waste waters contaminated with heavy metal.

It is also possible to use the inventive peptides to concentrate valuable metals from aqueous solutions.

Furthermore, peptides of the invention, which are loaded with heavy metal, can be used to obtain corresponding antibodies, which, in turn, themselves are used as a diagnostic aid for the degree of contamination of plants with heavy metals.

In addition, the homo-phytochelatins, which are loaded with radioactive metal and coupled to antibodies, can be used as diagnostic aids (for example, tumor diagnosis).

The present invention will now be described more fully by the following examples. It should, however, be pointed out that the following examples are for purposes of illustration only and are not intended to define the limits or scope of the invention.

EXAMPLE 1

1,000 g (corresponding to 54 g dry weight) of a cell culture of *Glycine max* were cultivated in 4 l of a 100 μmolar aqueous cadmium sulfate solution, shaken continuously for 3 days. The cell culture was then harvested, washed with distilled water and frozen in liquid nitrogen. The cell culture, which had been disrupted in this way, was then suspended in 500 ml of buffer solution (10 mmolar aqueous solution of trihydroxymethylaminomethane/HCl/2-mercaptoethanol) of pH=8.6.

The suspension was centrifuged. The supernatant was again brought to pH 8.6 and diluted until the conductivity was <1 kS. The supernatant was then loaded onto an ion exchanger column (diethylaminoethyl-agarose column, Bio-Rad, Richmond, Va., USA).

Subsequently, elution with an aqueous solution (0.5 moles/l NaCl, 10 mmoles/l trihydroxymethylaminomethane/HCL, pH=8.6) was carried out. For protein precipitation, solid ammonium sulfate was added to 85% saturation of the eluate. The mixture was then centrifuged, and the supernatant was freed of ammonium sulfate by ultrafiltration (YM-2 membrane supplied by Amicon Davers, GB) and concentrated to 15 ml.

Finally, the concentrated solution was subjected to gel filtration (Sephadex G-50, supplied by Pharmacia, Uppsala, Sweden) at pH=7. The pH was adjusted to this with ammonium acetate. Elution with 5 mmolar ammonium acetate solution produced initially a small amount of high molecular-weight protein and then the desired peptides. 180 mg of peptide mixture were obtained after freeze-drying of the eluate. The cadmium content was 13.8% by weight.

EXAMPLE 2

100 mg of the homo-phytochelatin mixture obtained as in Example 1 was dissolved in 10 ml of 0.01 normal hydrochloric acid. Gaseous hydrogen sulfide was passed into this solution to precipitate cadmium sulfide. This was then removed by centrifugation, and the supernatant was freeze-dried. 82 mg of metal-free peptide mixture were obtained.

The peptide mixture was fractioned by HPL chromatography on a reversed phase column (Nucleosil C-18 supplied by Macherey and Nagel, D,üren, FRG). It has the following composition:

46.3 mole% $(\gamma\text{-Glu-Cys})_2\beta\text{-Ala}$
37.8 mole% $(\gamma\text{-Glu-Cys})_3\beta\text{-Ala}$
11.7 mole% $(\gamma\text{-Glu-Cys})_4\beta\text{-Ala}$
3.6 mole% $(\gamma\text{-Glu-Cys})_5\beta\text{-Ala}$
0.3 mole% $(\gamma\text{-Glu-Cys})_6\beta\text{-Ala}$
0.3 mole% $(\gamma\text{-Glu-Cys})_{7-11}\beta\text{-Ala}$.

EXAMPLE 3

50 mg of the metal-free peptide mixture (from Example 2) were reduced with sodium borohydride and the product was taken up in 10 ml of 0.01 normal hydrochloric acid, and 250 μmole of iron sulfate in the form of a 1 molar solution were added. The operations were carried out under an atmosphere of nitrogen. The mixture was then neutralized (pH=7.5) with 0.01 normal sodium hydroxide solution. The solution thus obtained was finally applied to an agarose column (Sephadex G-25, Pharmacia, Uppsala, Sweden). After elution with water and freeze-drying of the eluate, a yield of 51 mg of peptide mixture loaded with iron was obtained.

While only several embodiments and examples of the present invention have been described, it will be obvious to those skilled in the art that many modifications may be made thereunto without departing from the spirit or scope of the present invention.

What is claimed is:

1. A peptide having the formula:

$$(\gamma\text{-Glu-Cys})_n\beta\text{-Ala},$$

wherein,
n is an integer from 2 to 11;
γ-Glu represents γ-glutamic acid;
Cys represents cysteine; and
β-Ala represents β-alanine.

2. The peptide according to claim 1, further having 1 to 4 moles of a metal cation per mole peptide.

3. The peptide according to claim 2, wherein said metal cation is capable of entering into a coordinative bond with a thiolate group of the peptide.

4. The peptide according to claim 3, wherein said metal cation is selected from the group consisting of lead, tin, bismuth, titanium, vanadium, molybdenum, manganese, cobalt, nickel, iron, copper, silver, gold, platinum, palladium, zinc, cadmium, mercury, uranium, arsenic, selenium, technetium and gallium.

* * * * *